(12) United States Patent
Suzuki

(10) Patent No.: US 11,266,547 B2
(45) Date of Patent: Mar. 8, 2022

(54) ABSORBENT ARTICLE

(71) Applicant: DAIO PAPER CORPORATION, Ehime (JP)

(72) Inventor: Yoko Suzuki, Tochigi (JP)

(73) Assignee: DAIO PAPER CORPORATION, Ehime (JP)

(*) Notice: Subject to any disclaimer, the term of this patent is extended or adjusted under 35 U.S.C. 154(b) by 636 days.

(21) Appl. No.: 16/301,896

(22) PCT Filed: Jun. 12, 2017

(86) PCT No.: PCT/JP2017/021590
§ 371 (c)(1),
(2) Date: Nov. 15, 2018

(87) PCT Pub. No.: WO2017/217354
PCT Pub. Date: Dec. 21, 2017

(65) Prior Publication Data
US 2019/0183693 A1    Jun. 20, 2019

(30) Foreign Application Priority Data

Jun. 14, 2016    (JP) .............................. JP2016-118276

(51) Int. Cl.
*A61F 13/15*        (2006.01)
*A61F 13/537*       (2006.01)
(Continued)

(52) U.S. Cl.
CPC .... *A61F 13/53747* (2013.01); *A61F 13/4704* (2013.01); *A61F 13/513* (2013.01);
(Continued)

(58) Field of Classification Search
CPC ............ A61F 13/53747; A61F 13/4704; A61F 13/5116; A61F 13/5125; A61F 13/513;
(Continued)

(56) References Cited

U.S. PATENT DOCUMENTS 5,554,145 A * 9/1996 Roe ................... A61F 13/49012
                                                     604/385.3
5,626,571 A * 5/1997 Young ..................... B32B 5/26
                                                       604/370
(Continued)

FOREIGN PATENT DOCUMENTS

CN         1582349      2/2005
CN       105592831      5/2016
(Continued)

OTHER PUBLICATIONS

International Search Report for PCT/JP2017/021590 dated Jul. 4, 2017.
(Continued)

*Primary Examiner* — Jacqueline F Stephens
(74) *Attorney, Agent, or Firm* — IPUSA, PLLC

(57) ABSTRACT

A liquid permeable surface sheet (3) includes an upper layer non-woven fabric (20) which is provided at the skin side, and which is hydrophilic, and a lower layer non-woven fabric (21) which is provided at the non-skin side, and which is water repellent. Multiple apertures (22) are formed which penetrate the upper layer non-woven fabric and the lower layer non-woven fabric. Accordingly, body fluid transfers smoothly through the apertures to an absorbent body. The upper layer non-woven fabric at the skin side is made to be hydrophilic such that body fluid readily permeates therethrough. The lower layer non-woven fabric at the non-skin side is made to be water repellent such that the body fluid which has passed through is not readily absorbed again. Accordingly, the backflow amount of body fluid can be reduced.

6 Claims, 3 Drawing Sheets

(51) Int. Cl.
*A61F 13/512* (2006.01)
*A61F 13/513* (2006.01)
*A61F 13/511* (2006.01)
*A61F 13/47* (2006.01)
*A61F 13/539* (2006.01)
*A61F 13/53* (2006.01)

(52) U.S. Cl.
CPC ...... *A61F 13/5116* (2013.01); *A61F 13/5125* (2013.01); *A61F 13/539* (2013.01); *A61F 13/511* (2013.01); *A61F 2013/4708* (2013.01); *A61F 2013/51178* (2013.01); *A61F 2013/530145* (2013.01); *A61F 2013/53782* (2013.01); *A61F 2013/53908* (2013.01)

(58) Field of Classification Search
CPC ...... A61F 13/539; A61F 13/51; A61F 13/511; A61F 13/5122; A61F 13/15707; A61F 13/512
See application file for complete search history.

(56) References Cited

U.S. PATENT DOCUMENTS

| | | | |
|---|---|---|---|
| 6,274,218 B1* | 8/2001 | Shimizu | A61F 13/512 428/137 |
| 6,461,716 B1* | 10/2002 | Lee | A61L 15/26 428/137 |
| 2003/0050618 A1* | 3/2003 | Kondo | A61F 13/537 604/383 |
| 2003/0093046 A1 | 5/2003 | Kim et al. | |
| 2004/0087924 A1 | 5/2004 | Sroda et al. | |
| 2004/0229008 A1* | 11/2004 | Hoying | B32B 27/32 428/92 |
| 2007/0078422 A1* | 4/2007 | Glaug | A61F 13/474 604/380 |
| 2016/0067118 A1 | 3/2016 | Hammons et al. | |
| 2016/0220421 A1 | 8/2016 | Kuramochi | |
| 2017/0112688 A1 | 4/2017 | Amano | |

FOREIGN PATENT DOCUMENTS

| | | |
|---|---|---|
| JP | 3587677 | 11/2004 |
| JP | 2006-149457 | 6/2006 |
| JP | 2009-118920 | 6/2009 |
| JP | 2009-118921 | 6/2009 |
| JP | 2010-005925 | 1/2010 |
| JP | 2011-055959 | 3/2011 |
| JP | 4792249 | 10/2011 |
| JP | 2016-019616 | 2/2016 |

OTHER PUBLICATIONS

Extended European Search Report for EP17813250.2 dated Feb. 28, 2019.
Chinese Office Action for CN201780031249.0 dated Aug. 4, 2020.

* cited by examiner (SKIN SIDE)

(NON-SKIN SIDE)

(SKIN SIDE)

(NON-SKIN SIDE)

ABSORBENT ARTICLE

TECHNICAL FIELD

The present invention relates to an absorbent article used mainly for sanitary napkins, pantyliners, incontinence pads, toiletries, etc., and specifically, to an absorbent article provided with a liquid permeable surface sheet formed of a two-layer structured apertured non-woven fabric.

BACKGROUND ART

Conventionally, as absorbent articles such as pantyliners, sanitary napkins, and incontinence pads, etc., there are known articles in which an absorbent body made of cotton-like pulp, etc., is interposed between a liquid impermeable back sheet such as a polyethylene sheet or a polyethylene sheet laminated non-woven fabric, and a liquid permeable surface sheet such as a non-woven fabric or a liquid permeable plastic sheet.

In particular, in a so-called night absorbent article to be worn during bedtime, the liquid permeable surface sheet requires various properties such as an absorption rate performance that quickly transfers body fluids such as blood and urine to the absorbent body; a liquid backflow preventing performance that prevents the body fluid once absorbed in the absorbent body from flowing back toward the skin; and furthermore, a smooth touch feeling, as the article is in direct contact with the skin.

As the surface material of the absorbent article, a liquid permeable non-woven fabric mainly formed of a non-woven fabric, and a porous plastic sheet are used; however, it has been difficult to achieve both high permeability of the body fluid and an anti-backflow property of the body fluid once absorbed.

As a conventional technique focusing on such absorbing performance and anti-backflow property, Patent Literature 1 below discloses a surface sheet in which apertures are formed to penetrate a non-woven fabric formed of a water repellent layer and a hydrophilic layer and the water repellent layer surface contacts the skin, and the surface sheet protrudes toward the absorbent body side from the surface of the hydrophilic layer on the absorbent body side, while the water repellent layer and the hydrophilic layer around the apertures are stretched such that the inner peripheral surfaces of the apertures are covered with fiber forming the water repellent layer.

Furthermore, Patent Literature 2 below discloses a surface sheet formed of a hydrophilic first fiber non-woven fabric and a hydrophilic second fiber non-woven fabric, in which the second fiber non-woven fabric has a higher density and higher hydrophilicity than the first fiber non-woven fabric, and the second fiber non-woven fabric is positioned below the first fiber non-woven fabric, and the opposing surfaces of the first and second fiber non-woven fabrics are intermittently joined via a hot melt adhesive, and at the peripheral walls of the apertures and in the vicinity thereof, the first and second fiber non-woven fabrics are integrated, such that the density of the surface sheet increases from the upper surface toward the lower surface thereof, and the density at the lower surface and in the vicinity thereof of the surface sheet is higher than the density of the second fiber non-woven fabric.

CITATION LIST

Patent Literature

[PTL 1]
Japanese Patent No. 4792249
[PTL 2]
Japanese Patent No. 3587677

SUMMARY OF INVENTION

Technical Problem

However, in the surface sheet described in Patent Literature 1, the skin-contacting surface of the surface sheet is the water repellent layer, and, therefore, when the wearer sleeps on his/her back or sleeps sideways, there has been a possibility that the body fluid travels along the surface of the surface sheet and side leakage occurs. Furthermore, the non-skin contacting surface of the surface sheet is a hydrophilic layer, and therefore the liquid tends to be retained in the hydrophilic layer, so that the body fluid is hardly transferred to the absorbent body, and the backflow amount tends to be large. Furthermore, in the above-described Patent Literature 2, both the first layer and the second layer of the surface sheet are hydrophilic, and, therefore, the liquid tends to be retained in the surface sheet and the body fluid is hardly transferred to the absorbent body, and the backflow amount tends to be large.

It is, therefore, a primary object of the present invention to provide an absorbent article capable of smoothly transferring body fluids to an absorbent body and reducing the backflow amount.

Solution to Problem

In order to solve the above problem, the present invention according to claim 1 provides an absorbent article in which an absorbent body is interposed between a liquid permeable surface sheet and a liquid impermeable back sheet, wherein the liquid permeable surface sheet includes an upper layer non-woven fabric having hydrophilicity disposed on a skin side, and a lower layer non-woven fabric having water repellency disposed on a non-skin side, and wherein multiple apertures, which penetrate the upper layer non-woven fabric and the lower layer non-woven fabric, are formed in the liquid permeable surface sheet.

In the present invention according to claim 1, multiple apertures are formed in the liquid permeable surface sheet, and therefore the body fluid can be smoothly transferred to the absorbent body through the apertures. Furthermore, the upper layer non-woven fabric disposed on the skin side has hydrophilicity that easily absorbs body fluid, and the lower layer non-woven fabric disposed on the non-skin side is made water-repellent such that the body fluid once passed through is hardly absorbed, and, therefore, the backflow amount of body fluid can be reduced.

The present invention according to claim 2 provides the absorbent article according to claim 1, wherein a fineness of the lower layer non-woven fabric is set to be lower than a fineness of the upper layer non-woven fabric.

In the present invention according to claim 2, fiber having a large fiber diameter is used for the layer on the skin side of the wearer, and fiber having a small fiber diameter is used for the layer on the absorbent body side, thereby generating a gradient in the capillary force, to improve the force of sucking the body fluid.

The present invention according to claim 3 provides the absorbent article according to claim 1 or 2, wherein an aperture ratio of the apertures is 10% to 25%.

In the present invention according to claim 3, the aperture ratio of the apertures is set to 10% to 25%. When the aperture ratio is lower than 10%, the amount of body fluid that passes through the apertures and moves to the absorbent body side decreases, and the liquid tends to remain on the surface, and when the aperture ratio is higher than 25%, the once absorbed body fluid tends to flow back toward the skin through the apertures.

The present invention according to claim 4 provides the absorbent article according to any one of claims 1 to 3, wherein a size of each of the apertures is 0.3 mm to 4.0 mm.

In the present invention according to claim 4, by forming the apertures to have a predetermined size, it is possible to eliminate liquid remaining on the surface and make it difficult for the liquid to flow back toward the skin.

The present invention according to claim 5 provides the absorbent article according to any one of claims 1 to 4, wherein a second sheet having hydrophilicity is disposed adjacent to a non-skin side of the liquid permeable surface sheet, and a fineness of the second sheet is set to be higher than a fineness of the liquid permeable surface sheet.

In the present invention according to claim 5, by making the fineness of the second sheet higher than the fineness of the liquid permeable surface sheet, the body fluid of the liquid permeable surface sheet can be smoothly transferred to the absorbent body.

Advantageous Effects of Invention

As described in detail above, according to the present invention, the body fluid can be smoothly transferred to the absorbent body, and the backflow amount can be reduced.

DESCRIPTION OF EMBODIMENTS

Figure 1:
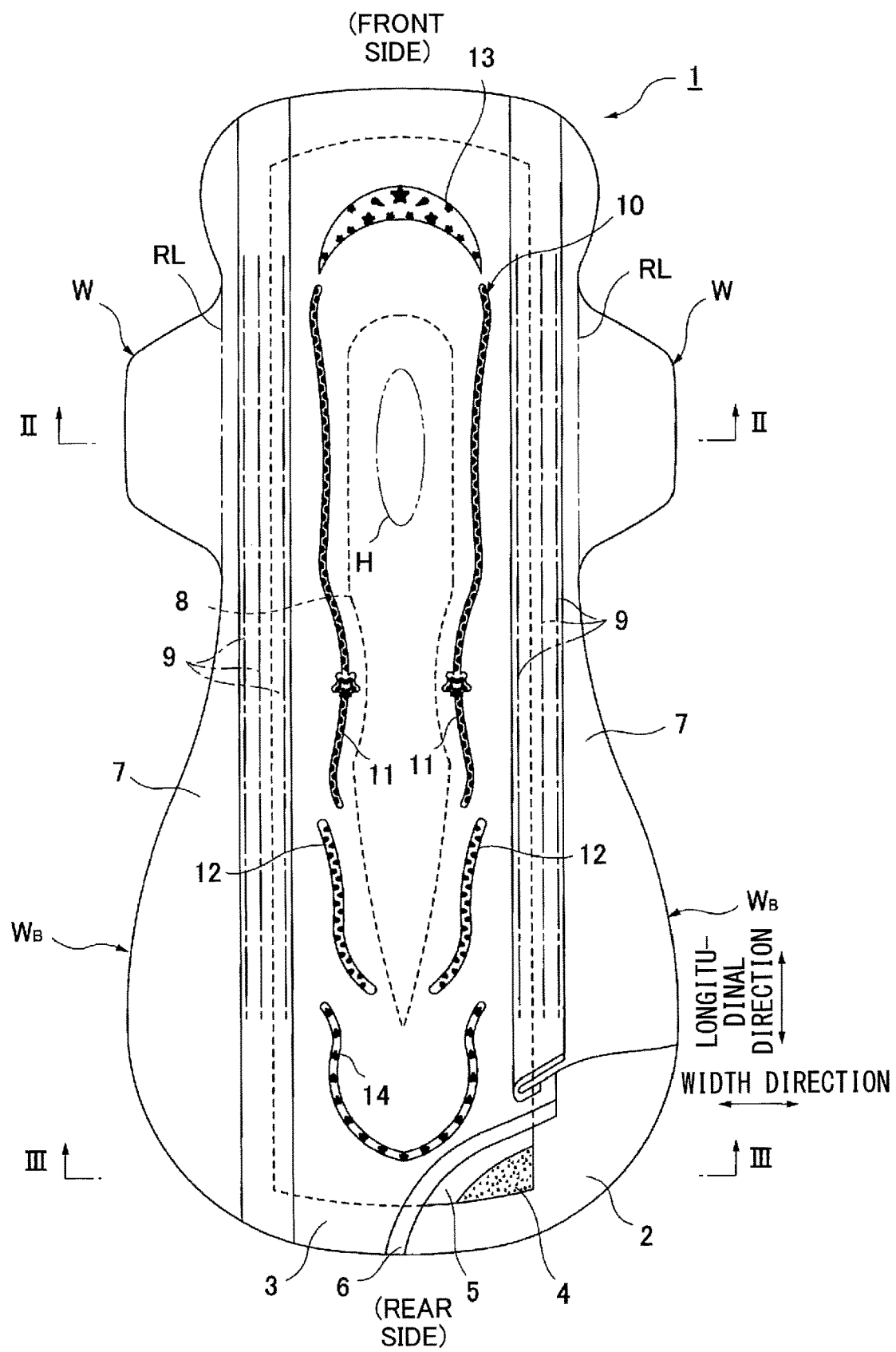
FIG. 1 is a partial cutaway development view of a sanitary napkin 1 according to the present invention.
Figure 2:
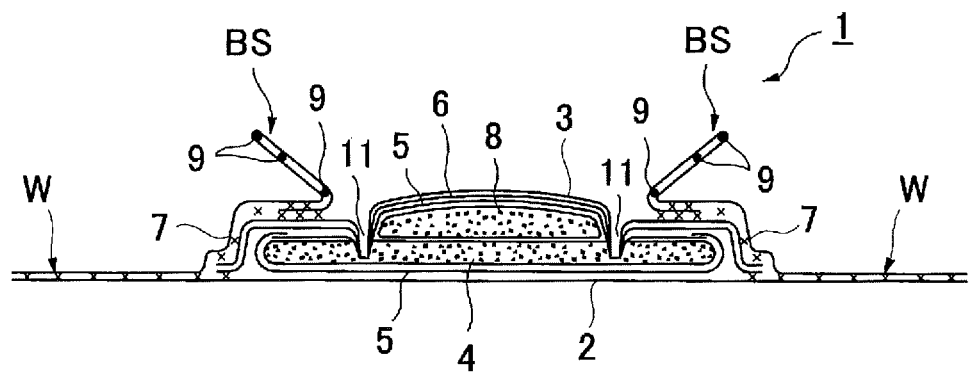
FIG. 2 is a view taken along an arrow line II-II of FIG. 1.

Hereinafter, embodiments of the present invention will be described in detail with reference to the drawings.
[Basic Structure of Sanitary Napkin 1]
As illustrated in FIGS. 1 and 2, a sanitary napkin 1 according to the present invention includes a liquid impermeable back sheet 2 formed of a polyethylene sheet, etc., a liquid permeable surface sheet 3 for quickly permeating menstrual blood and vaginal discharge, etc. (hereinafter collectively referred to as "body fluid"), an absorbent body 4 formed of cotton-like pulp or synthetic pulp interposed between these sheets 2 and 3, a second sheet 6 formed of a hydrophilic non-woven fabric disposed adjacent to the non-skin side of the liquid permeable surface sheet 3, and a side non-woven fabric 7 provided on both side portions of the skin contact surface side across substantially the entire length along the longitudinal direction. Around the absorbent body 4, at the upper and lower edge portions thereof, the outer edge portions of the liquid impermeable back sheet 2 and the liquid permeable surface sheet 3 are joined by a joining means such as an adhesive such as hot melt, a heat seal, and an ultrasonic seal, etc., and at both side edge portions around the absorbent body 4, the outer edge portions of the liquid impermeable back sheet 2 extended sideways beyond the absorbent body 4 and the side non-woven fabric 7 are joined by a joining means such as an adhesive such as hot melt, a heat seal, and an ultrasonic seal, etc., and, therefore, a flap portion where the absorbent body does not intervene, is formed. Note that in the illustrated example, in order to maintain the shape of the absorbent body 4 and to improve the diffusibility of the absorbent body 4, the absorbent body 4 is surrounded by an encapsulating sheet 5 formed of crepe paper or non-woven fabric, etc.; however, the encapsulating sheet 5 is not required to be provided.

Hereinafter, the structure of the sanitary napkin 1 will be described in detail. As the liquid impermeable back sheet 2, a sheet material that has at least a water-impermeable property, such as polyethylene, etc., is used; however, from the viewpoint of preventing steaming, it is desirable to use a material having moisture permeability. As this water-impermeable/moisture-permeable sheet material, a microporous sheet obtained by melt-kneading an inorganic filler in an olefin-based resin such as polyethylene or polypropylene, etc., for molding a sheet and then stretching the sheet in a uniaxial direction or biaxial direction, is suitably used. One or a plurality of adhesive layers (not illustrated) are formed along the longitudinal direction of the napkin on the non-skin side surface (outer surface) of the liquid impermeable back sheet 2, so as to fix the sanitary napkin 1 to underwear when the sanitary napkin 1 is worn on the body. As the liquid impermeable back sheet 2, a poly-laminate non-woven fabric in which a plastic film and a non-woven fabric are laminated, may be used.

The absorbent body 4 interposed between the liquid impermeable back sheet 2 and the liquid permeable surface sheet 3 is formed of, for example, cotton-like pulp and a water-absorbent polymer. The water-absorbent polymer is mixed, for example, as granular powder, in the pulp constituting the absorbent body. Examples of the pulp include cellulose fiber such as chemical pulp and dissolved pulp obtained from wood, and artificial cellulose fiber such as rayon and acetate, etc., and softwood pulp having a longer fiber length than hardwood pulp is suitably used in terms of function and price. The fabric weight (basis weight) of the absorbent body 4 is preferably 250 g/m$^2$ to 650 g/m$^2$, and more preferably 300 g/m$^2$ to 400 g/m$^2$.

Furthermore, synthetic fiber may be mixed in the absorbent body 4. As the synthetic fiber, polyolefin-based fiber such as polyethylene or polypropylene, etc., polyester-based fiber such as polyethylene terephthalate and polybutylene terephthalate, etc., polyamide-based fiber such as nylon, or copolymers thereof, etc., may be used, or a mixture of two types of these fibers may be used. Furthermore, composite fiber such as core-sheath type fiber having a core made of fiber with a high melting point and a sheath made of fiber with a low melting point, side-by-side type fiber, and splittable fiber, may be used. With respect to synthetic fiber, in the case of hydrophobic fiber, it is desirable to use a fiber that is surface-treated with a hydrophilizing agent so as to have hydrophilicity for body fluids.

As illustrated in FIGS. 1 and 2, it is preferable to provide a middle-high portion 8 of the absorbent body thickened on the skin side in a region, including a portion corresponding to a body fluid excretion part H, of the absorbent body 4. The middle-high portion 8 is adjacent to the skin side surface of the absorbent body 4, and is disposed at the center in the width direction of the absorbent body 4, and is formed to be smaller in the width dimension and the longitudinal dimension than the absorbent body 4. If the middle-high portion 8 is too thick, the rigidity increases and the adhesion to the body decreases, whereas if the middle-high portion 8 is too thin, the adhesion with the body fluid excretion part H of the wearer decreases, and, therefore, the thickness of the middle-high portion 8 is to be 3 mm to 25 mm, preferably 5 mm to 18 mm. The total fabric weight of the absorbent body 4 in the region where the middle-high portion 8 is disposed and the middle-high portion 8, is to be 400 g/m² to 900 g/m², preferably 600 g/m² to 800 g/m².

The middle-high portion 8 is disposed at least in a region including a portion corresponding to the body fluid excretion part H of the wearer. The middle-high portion 8 may be formed to have an elongated shape continuing from a region including a portion corresponding to the body fluid excretion part H to a region including a portion corresponding to the intergluteal cleft as in the illustrated example, or may be disposed only in a region including a portion corresponding to the body fluid excretion part H and not disposed in a region including a portion corresponding to the intergluteal cleft on the rear side from the body fluid excretion part H.

Figure 3:
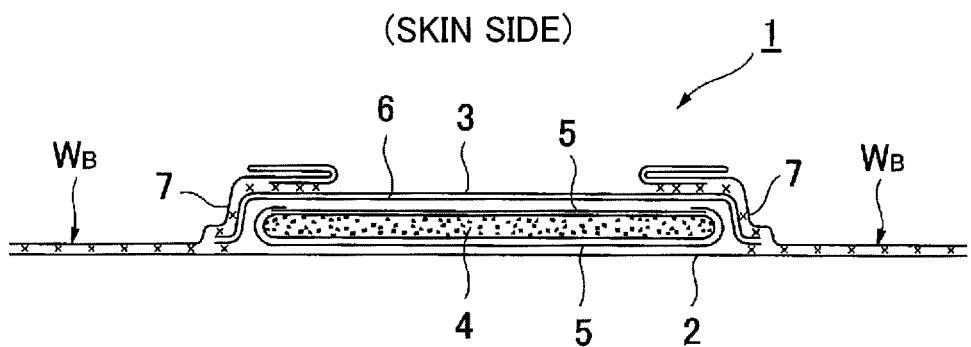
FIG. 3 is a view taken along an arrow line III-III of FIG. 1.

In the illustrated example, the width dimension of the liquid permeable surface sheet 3 is slightly longer than the width of the absorbent body 4 as illustrated in the cross sectional views of FIGS. 2 and 3, and only covers the absorbent body 4, and at the outer sides thereof, the side non-woven fabric 7 separate from the liquid permeable surface sheet 3 is disposed. The side non-woven fabric 7 is formed by using a non-woven fabric that has undergone appropriate water repellent treatment or hydrophilic treatment, according to the purpose, such as preventing menstrual blood and vaginal discharge, etc., from penetrating, or enhancing the touching feeling on the skin, etc. The side non-woven fabric 7 may be formed of a material such as natural fiber, synthetic fiber, and regenerated fiber, etc., by an appropriate processing method; however, in order to eliminate the sense of roughness and to prevent steaming, it is preferable to use non-woven fabric having reduced fabric weight and having air permeability. Specifically, it is desirable to use non-woven fabric fabricated to have a fabric weight of 13 g/m² to 23 g/m², and in order to reliably prevent the permeation of body fluids, water repellent treated non-woven fabric coated with a silicon-based, paraffin-based, or alkyl chromic chloride-based water repellent, etc., is suitably used.

As illustrated in FIGS. 2 and 3, the side non-woven fabric 7 has a structure in which the outer portion of the side non-woven fabric 7 from the widthwise intermediate portion, is adhered, by an adhesive such as hot melt, to a range extending from a predetermined inner position to the outer edge of the liquid impermeable back sheet 2, so that a flap portion in which the absorbent body 4 does not intervene, is formed on both side portions of the absorbent body 4, by the laminated sheet portion of the side non-woven fabric 7 and the liquid impermeable back sheet 2. By this flap portion, a pair of right and left wing-shaped flaps W, W is formed at positions of the absorbent body side portions substantially corresponding to the body fluid excretion part H, and hip-holding flaps $W_B$, $W_B$ can be formed at positions on the buttock side (rear side) thereof. An adhesive layer (not illustrated) is provided on the outer surface side of the wing-shaped flaps W, W and the hip-holding flaps $W_B$, $W_B$, respectively. When attaching the sanitary napkin 1 to shorts, the wing-shaped flaps W, W are folded back to the opposite side at the positions of fold lines RL of the base end part, and wrapped around the crotch part of the shorts to be fastened, and the hip-holding flaps $W_B$, $W_B$ are fastened to the inner face of the shorts.

On the other hand, the inner side portion of the side non-woven fabric 7 is folded back to be almost two-fold, and inside this double sheet portion, one or more, or three in the illustrated example, threadlike elastically extensible members 9, 9 . . . are disposed in a state where both ends or appropriate positions in the longitudinal direction are fixed to the intermediate portion in the height direction of the side non-woven fabric 7. As illustrated in FIG. 3, at the front and rear end portions, the double sheet portion is adhered to the absorbent body 4 side in a state where the side non-woven fabric 7 is folded once outside to be laminated, whereby as illustrated in FIG. 2, linear standing gathers BS, BS standing on the surface side while tilting toward the outside are formed as a pair on the right and left sides.

In the sanitary napkin 1, a compressed groove 10 recessed from the outer surface side of the liquid permeable surface sheet 3 toward the liquid impermeable back sheet 2, is formed at a position of the outer side portion in the vicinity of the middle-high portion 8. The compressed groove 10 is formed on both side portions from at least a region including a portion corresponding to the body fluid excretion part H to a region including a portion corresponding to the intergluteal cleft. Specifically, in the example illustrated in FIG. 1, on both side portions from a region including a portion corresponding to the body fluid excretion part H to a region including the portion corresponding to the intergluteal cleft, the compressed grooves 10 are formed of front side longitudinal compressed grooves 11, 11 continuously formed along the substantially longitudinal direction of the sanitary napkin 1, rear side longitudinal compressed grooves 12, 12 that are disposed on the rear side of and spaced apart from the front side longitudinal compressed grooves 11, 11 and that are continuously formed along substantially the longitudinal direction of the sanitary napkin 1 at both sides of the portion corresponding to the rear end portions of the intergluteal cleft, a front end crescent shaped compressed groove 13 that is disposed in front of and spaced apart from the front side longitudinal compressed grooves 11, 11 and that is formed in a crescent shape substantially along the width direction of the sanitary napkin 1 and that transverses the longitudinal center line of the sanitary napkin 1 in the width direction, and a rear end curved shaped compressed groove 14 that is disposed on the rear side of and spaced apart from the rear side longitudinal compressed grooves 12, 12 and that is formed in a curved shape that bulges toward the rear and that transverses the longitudinal center line of the sanitary napkin 1 in the width direction. The compressed groove 10 is formed by integrally compressing a portion from the liquid permeable surface sheet 3 to the absorbent body 4, by thermal embossment from the outer surface side of the liquid permeable surface sheet 3.

[Liquid Permeable Surface Sheet 3]

Figure 4:
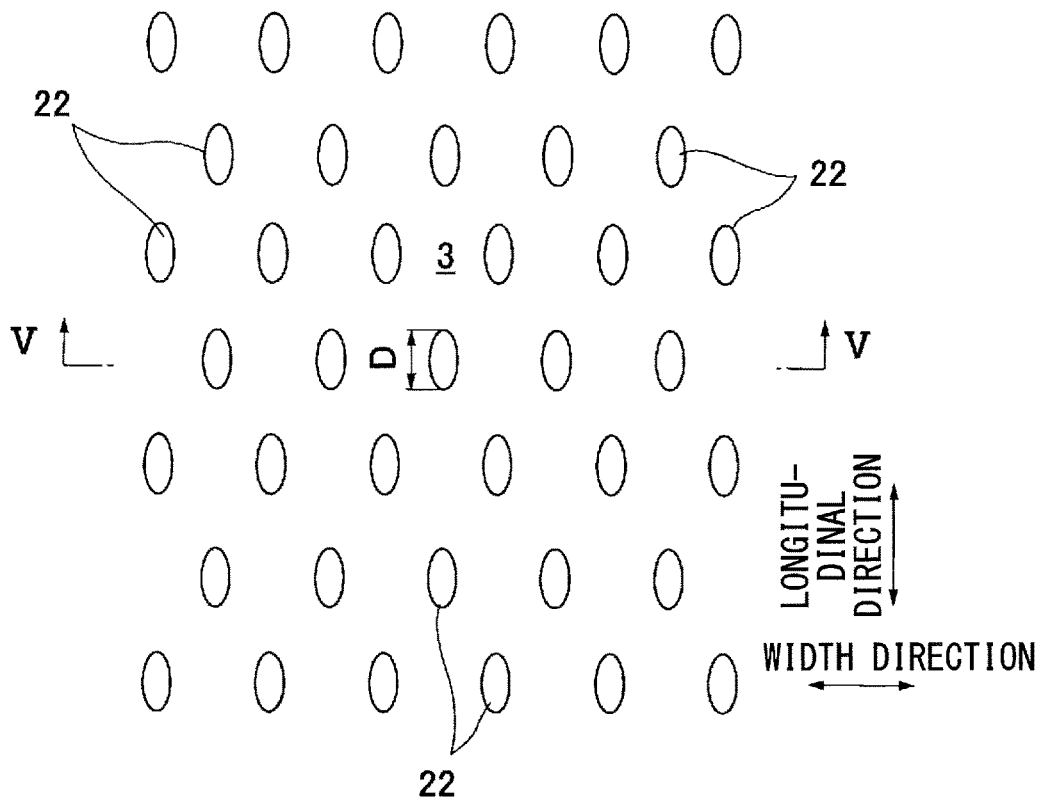
FIG. 4 is an enlarged plan view of a liquid permeable surface sheet 3.
Figure 5:
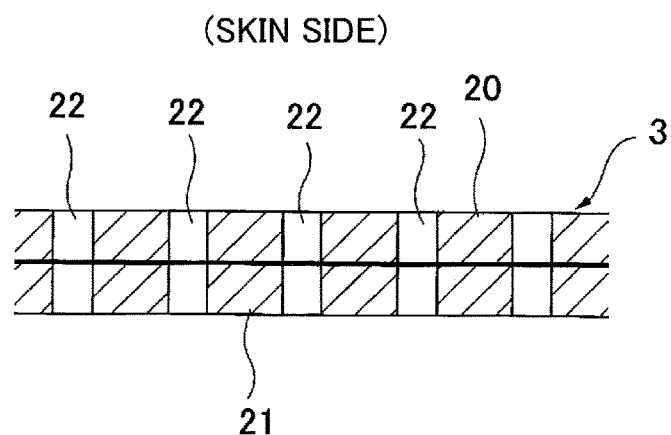
FIG. 5 is an enlarged cross-sectional view of the liquid permeable surface sheet 3 (a view taken along an arrow line V-V of FIG. 4).

Next, the liquid permeable surface sheet 3 will be described in detail. As illustrated in FIGS. 4 and 5 in detail, the liquid permeable surface sheet 3 has a two-layered structure including an upper layer non-woven fabric 20 having hydrophilicity disposed on the skin side and a lower layer non-woven fabric 21 having water repellency disposed on the non-skin side, and a large number of apertures 22, 22 . . . , penetrating the upper layer non-woven fabric 20 and the lower layer non-woven fabric 21, are formed. As the material fiber forming the non-woven fabric, in addition to synthetic fiber such as olefin-based, polyester-based, and polyamide-based fiber, etc., such as polyethylene or polypropylene, etc., regenerated fiber such as rayon or cupra, etc., and natural fiber such as cotton, may be used. The non-woven fabric may be obtained by appropriate processing methods such as an air-through method, a spun lace method, a spun bond method, a thermal bonding method, a melt blown method, and a needle punching method, etc. Among these processing methods, the non-woven fabric produced by the air-through method has large spaces between the fibers and has a soft feeling, and is bulky, so that the fabric has a good fitting feeling, and the body fluid tends to penetrate easily through the fiber, which is preferable. The fiber of the non-woven fabric may be either of long fiber or short fiber; however, short fiber is preferably used for giving the texture of toweling. Furthermore, in order to facilitate the embossing treatment, it is preferable to use an olefin-based fiber such as polyethylene or polypropylene having a relatively low melting point. It is also possible to suitably use composite fiber such as core-sheath type fiber having a core made of fiber with a high melting point and a sheath made of fiber with a low melting point, side-by-side type fiber, and splittable fiber.

As the upper layer non-woven fabric 20, a material having hydrophilicity may be used, such as regenerated fiber such as rayon and cupra, and natural fiber such as cotton, or synthetic fiber such as olefin-based fiber such as polyethylene or polypropylene, polyester-based fiber, or polyamide-based fiber, may be surface-treated with a hydrophilic agent to have hydrophilicity. Examples of the hydrophilic agent include anionic surfactants, carboxylate salts, acylated hydrolyzed proteins, sulfonate salts, sulfate ester salts, phosphate ester salts, nonionic surfactants, polyoxyethylene-based surfactants, carboxylic acid esters, carboxylic acid amides, polyalkyleneoxide block copolymers, cationic surfactants, quaternary ammonium salts, amphoteric surfactants, and imidazolinium derivatives, etc. Other than these, any known hydrophilic agent that can be applied on the surface of the fiber may be used. The hydrophilic agent may be applied only on the skin side surface of the upper layer non-woven fabric 20 or on both the skin side surface and the non-skin side surface of the upper layer non-woven fabric 20. By subjecting at least the skin side surface to hydrophilic treatment, at least the skin side surface of the upper layer non-woven fabric 20 becomes hydrophilic, and body fluid is easily absorbed into the liquid permeable surface sheet 3.

As the lower layer non-woven fabric 21, it is preferable to use a material having water repellency by using synthetic fiber such as olefin-based fiber, polyester-based fiber, and polyamide-based fiber, etc., such as polyethylene or polypropylene; however, when using a non-woven fabric of hydrophilic fiber such as cotton fiber, a water repellent agent is externally applied before usage. Among known water repellent agents such as paraffin-based and silicone-based agents, those that are less irritating to the skin may be appropriately selected and used; however, it is preferable to appropriately select less irritating oils and fats such as stearic acid amide, zinc stearate, calcium stearate, stearin acid diethanol amide, and magnesium stearate, etc., and other than these, any known water repellent agent that can be applied to fiber may be used. The water repellent agent may be applied only on the non-skin side surface of the lower layer non-woven fabric 21 or on both the non-skin side surface and the skin side surface. By subjecting at least the non-skin side surface to water repellent treatment, at least the non-skin side surface of the lower layer non-woven fabric 21 becomes water repellent, so that the body fluid once absorbed on the absorbent body side can be prevented from flowing back to the liquid permeable surface sheet 3.

As illustrated in FIG. 5, multiple apertures 22, 22 . . . penetrating the upper layer non-woven fabric 20 and the lower layer non-woven fabric 21 are formed by performing an aperture treatment in a state where the upper layer non-woven fabric 20 and the lower layer non-woven fabric 21 are laminated, so that the apertures 22 integrally penetrate the upper layer non-woven fabric 20 and the lower layer non-woven fabric 21. That is, the apertures 22 continuously penetrate the skin side surface of the upper layer non-woven fabric 20 to the non-skin side surface of the lower layer non-woven fabric 21. Therefore, the body fluid can pass through the apertures 22 from the skin side to the non-skin side of the liquid permeable surface sheet 3, and the liquid can smoothly transfer to the absorbent body 4 side. The aperture treatment may be performed by a method of piercing the fabric with a heating needle, or by a method of softening the liquid permeable surface sheet 3 to near the softening temperature, positioning the liquid permeable surface sheet 3 on the upper surface of a support body having multiple apertures, and applying suction to the liquid permeable surface sheet 3 from under the support body, or applying air pressure from the upper surface of the support body with air pressure, etc., to form the apertures.

In the sanitary napkin 1 having the above configuration, multiple apertures 22, 22 . . . are formed in the liquid permeable surface sheet 3, and, therefore, body fluid is smoothly transferred to the absorbent body 4 through these apertures 22, 22 . . . . Furthermore, the upper layer non-woven fabric 20 disposed on the skin side has hydrophilicity, thus making it easy for the body fluid to be absorbed, and the lower layer non-woven fabric 21 disposed on the non-skin side is water repellent, and thus hardly absorbs the body fluid that has once passed through, so that the body fluid once absorbed in the absorbent body 4 side is blocked by the lower layer non-woven fabric 21 that is water repellent, and, therefore, it is possible to reduce body fluid flowing back to the skin side of the liquid permeable surface sheet 3.

In order to further facilitate the transfer of body fluid from the liquid permeable surface sheet 3 to the absorbent body side, the fineness of the lower layer non-woven fabric 21 is preferably set to be lower than the fineness of the fiber of the upper layer non-woven fabric 20. Accordingly, the force of sucking the body fluid due to the capillary phenomenon is larger in the lower layer non-woven fabric 21 having a lower fineness, so that a gradient is generated in the capillary force, and the force of sucking the body fluid is enhanced. Specifically, the fineness of the upper layer non-woven fabric 20 is preferably 2.0 dtex to 6.0 dtex, and the fineness of the lower layer non-woven fabric 21 is preferably 1.0 dtex to 5.0 dtex. The difference between the fineness of the upper layer non-woven fabric 20 and the fineness of the lower layer non-woven fabric 21 is to be 1.0 dtex to 5.0 dtex, preferably 2.5 dtex to 5.0 dtex, in order to ensure a capillary force gradient.

The ratio (weight ratio) of the upper layer non-woven fabric 20 and the lower layer non-woven fabric 21 is set as "upper layer non-woven fabric 20:lower layer non-woven fabric 21" being 2:8 to 8:2, preferably 4:6 to 6:4, more preferably 5:5. By making the ratio of the upper layer non-woven fabric 20 and the lower layer non-woven fabric 21 substantially equal, it becomes possible to more reliably absorb body fluid and prevent backflow of body fluid.

The range in which the lower layer non-woven fabric 21 has water repellency is preferably the entire surface of the lower layer non-woven fabric 21. However, for example, in a range including a portion corresponding to the body fluid excretion part H of the wearer, the amount of water absorption is large and backflow tends to occur. Therefore, the water repellency may be partially applied, for example, by making the central portion in the width direction including the middle-high portion 8 have water repellency and making both side portions thereof have hydrophilicity.

The aperture ratio of the apertures 22 . . . is preferably 10% to 25%. The aperture ratio is the ratio of the area occupied by the apertures 22 . . . portion per unit area of the liquid permeable surface sheet 3. If the aperture ratio is lower than 10%, the amount of body fluid that passes through the apertures 22 . . . and moves toward the absorbent body 4 decreases, and the liquid tends to remain on the surface. Furthermore, when the aperture ratio is larger than 25%, the body fluid once absorbed in the absorbent body 4 tends to easily flow back through the apertures 22 . . . .

The multiple apertures 22 . . . may be formed over the entire surface of the liquid permeable surface sheet 3, or may be formed only in a region including a portion corresponding to the body fluid excretion part and apertures may not be formed in other regions. Furthermore, the apertures 22 . . . may be arranged in a pattern having regularity such as a staggered shape as illustrated in FIG. 4 or a positive grid shape, or may be arranged in a random pattern without such regularity.

As illustrated in FIG. 4, the planar shape of each of the apertures 22 . . . may be a long oval shape in the napkin longitudinal direction, or may be a long oval shape in the napkin width direction, a circular shape, an oval shape, or a rectangular shape, etc., although not illustrated.

In this case, it is preferable that a size D of the apertures 22 . . . is 0.3 mm to 4.0 mm, preferably 0.5 mm to 2.8 mm. Here, the size D of the aperture 22 is the maximum dimension of the aperture 22 in the planar direction, as illustrated in FIG. 4. When the size of the aperture 22 is less than 0.3 mm, it is difficult for the body fluid to pass through the aperture 22, and when the size of the aperture 22 exceeds 4.0 mm, the body fluid is liable to flow back toward the skin.

[Second Sheet 6]

Next, the hydrophilic second sheet 6 disposed adjacent to the non-skin side of the liquid permeable surface sheet 3 will be described. The second sheet 6 may be any kind of sheet that has hydrophilicity to body fluids. Specifically, a material having hydrophilicity may be used by using regenerated fiber such as rayon and cupra, and natural fiber such as cotton, or a fiber having hydrophilicity may be used, which is obtained by performing surface-treatment with a hydrophilic agent on synthetic fiber such as olefin-based fiber such as polyethylene or polypropylene, polyester-based fiber, or polyamide-based fiber.

The second sheet 6 is disposed between the liquid permeable surface sheet 3 and the absorbent body 4. The second sheet 6 may be disposed at least in a range covering the absorbent body 4; however, it is preferable to provide the second sheet 6 in substantially the same range as the liquid permeable surface sheet 3. It is desirable that the second sheet 6 is discontinuously bonded to the liquid permeable surface sheet 3 by hot melt or thermal fusion (embossing).

The fineness of the second sheet 6 is preferably set to be higher than the fineness of the liquid permeable surface sheet 3. If the fineness of the second sheet 6 is almost equal to or lower than that of the liquid permeable surface sheet 3, the difference from the fineness of the lower layer non-woven fabric 21 will be small, and it will be difficult for the body fluid to transfer from the liquid permeable surface sheet 3 to the second sheet 6. On the other hand, by making the fineness of the second sheet 6 higher than the fineness of the liquid permeable surface sheet 3, the liquid can be smoothly transferred to the absorbent body 4. The fineness of the second sheet 6 is preferably 2.0 dtex to 6.0 dtex.

As the second sheet 6, a nonporous non-woven fabric may be used, or a non-woven fabric in which apertures are formed in a predetermined pattern may be used. In the case of forming the apertures, the apertures formed in the second sheet 6 and the apertures 22 . . . formed in the liquid permeable surface sheet 3 may be patterns that do not coincide with each other at all, or may be patterns that partially or entirely coincide with each other.

EXAMPLES

A comparison test with respect to the backflow amount was carried out by using the sanitary napkin 1 having the upper layer non-woven fabric 20 that is hydrophilic and the lower layer non-woven fabric 21 that is water repellent, and a conventional sanitary napkin in which both the upper layer non-woven fabric and the lower layer non-woven fabric are hydrophilic. In the test of the backflow amount, 3 cc of artificial menstrual blood at 37° C. was injected 5 times at 3 minute intervals on the napkin, and 1 minute after the 5th injection of artificial menstrual blood, a filter paper whose weight has been measured in advance was placed on the napkin, a weight of 5 g/m² load was loaded on the filter paper for 5 minutes, the weight of the filter paper was measured again after loading, and the backflow amount (g) was calculated from the difference in the weight of the filter paper before and after loading.

Note that as the ingredients in 1 liter of the artificial menstrual blood, 100 ml of glycerin, 4.6 g of CMC (carboxymethylcellulose sodium), 875 ml of purified water, 10 g of sodium chloride, and 10.7 g of sodium carbonate were used. Furthermore, the fabric weight of each of the upper layer non-woven fabric and the lower layer non-woven fabric was 11 g/m², the size of the aperture was 1.2 mm to 1.4 mm in the longitudinal direction, and 0.9 mm to 1.0 mm in the width direction, the aperture ratio was 18% to 20%, and the fiber structure was PE/PET.

TABLE 1

| | | Comparative example 1 | Example 1 | Comparative example 2 | Example 2 |
|---|---|---|---|---|---|
| Surface material | Upper layer nonwoven fabric | Weak hydrophilicity 6.0 dtex | Weak hydrophilicity 6.0 dtex | Weak hydrophilicity mixed cotton 2.0 dtex + 6.0 dtex | Weak hydrophilicity mixed cotton 2.0 dtex + 6.0 dtex |
| | Lower layer nonwoven fabric | Hydrophilicity 2.0 dtex | Water-repellency 2.0 dtex | Hydrophilicity 2.0 dtex | Water-repellency 2.0 dtex |
| Backflow amount (g) | | 0.090 | 0.056 | 0.147 | 0.133 |

Comparing comparative example 1 with example 1, and comparing comparative example 2 with example 2, the backflow amount decreased when the lower layer non-woven fabric is water repellent. That is, it was demonstrated that the backflow amount can be reduced, when the upper layer of the liquid permeable surface sheet 3 is hydrophilic so that the body fluid is easily absorbed, and the lower layer of the liquid permeable surface sheet 3 is water repellent so that the once absorbed body fluid does not flow back toward the skin.

REFERENCE SIGNS LIST

1 ... sanitary napkin, 2 ... liquid impermeable back sheet, 3 ... liquid permeable surface sheet, 4 ... absorbent body, 5 ... encapsulating sheet, 6 ... second sheet, 7 ... side non-woven fabric, 8 ... middle-high portion, 9 ... threadlike elastically extensible members, 10 ... compressed groove, 11 ... front side longitudinal compressed groove, 12 ... rear side longitudinal compressed groove, 13 ... front end crescent shaped compressed groove, 14 ... rear end curved shaped compressed groove, 20 ... upper layer non-woven fabric, 21 ... lower layer non-woven fabric, 22 ... apertures

The invention claimed is:

1. An absorbent article in which an absorbent body is interposed between a liquid permeable surface sheet and a liquid impermeable back sheet, wherein
   the liquid permeable surface sheet includes
      an upper layer non-woven fabric having hydrophilicity disposed on a skin side, and
      a lower layer non-woven fabric having water repellency disposed on a non-skin side, and wherein
   multiple apertures, which integrally penetrate the upper layer non-woven fabric and the lower layer non-woven fabric so that each of the apertures has an identical diameter in the upper layer non-woven fabric and the lower layer non-woven fabric, are formed in the liquid permeable surface sheet,
   wherein the absorbent body includes a middle-high portion disposed at a center in a width direction of the absorbent body on the skin side, and
   wherein the lower layer non-woven fabric has the water repellency in a center portion including the middle-high portion and hydrophilicity in portions that are located outside the center portion in the width direction of the absorbent body.

2. The absorbent article according to claim 1, wherein a fineness of the lower layer non-woven fabric is set to be lower than a fineness of the upper layer non-woven fabric.

3. The absorbent article according to claim 1, wherein an aperture ratio of the apertures is 10% to 25%.

4. The absorbent article according to claim 1, wherein a size of each of the apertures is 0.3 mm to 4.0 mm.

5. The absorbent article according to claim 1, wherein
   a second sheet having hydrophilicity is disposed adjacent to a non-skin side of the liquid permeable surface sheet, and
   a fineness of the second sheet is set to be higher than a fineness of the liquid permeable surface sheet.

6. The absorbent article according to claim 1, wherein the apertures are formed only in a region corresponding to a body fluid excretion part and not formed in other regions.

* * * * *